United States Patent [19]

Freche et al.

[11] 4,195,918
[45] Apr. 1, 1980

[54] ILLUMINATING SPECTACLES WITH VARIABLE MAGNIFYING POWER

[76] Inventors: Charles Freche, 9 rue Villebois Mareuil, 75017 Paris; Jacques Lotteau, 22, rue de Breteuil, 78670 Villennes sur Seine, both of France

[21] Appl. No.: 954,731

[22] Filed: Oct. 20, 1978

[30] Foreign Application Priority Data

Nov. 14, 1977 [FR] France ............................. 77 34106

[51] Int. Cl.² .................. G02B 23/18; G02B 25/02
[52] U.S. Cl. .......................................... 351/158; 128/3; 128/380; 350/145; 362/32
[58] Field of Search .................. 351/158, 41, 45, 46; 128/380, 360, 3; 240/2, 59, 5; 350/73, 146, 145; 179/109; 2/12-14; 362/32

[56] References Cited
U.S. PATENT DOCUMENTS

| | | | |
|---|---|---|---|
| 1,785,448 | 12/1930 | Hugershoff | 350/145 |
| 2,826,114 | 3/1958 | Bryan | 350/145 |
| 3,449,043 | 6/1969 | Houston | 351/158 |
| 3,592,525 | 7/1971 | Schultz | 351/158 |
| 4,086,004 | 4/1978 | Scrivo et al. | 351/158 |

*Primary Examiner*—John K. Corbin
*Assistant Examiner*—B. Wm. de los Reyes
*Attorney, Agent, or Firm*—Fisher, Christen & Sabol

[57] ABSTRACT

The invention relates to illuminating spectacles with variable magnifying power, essentially comprising, in combination, a frame 1, provided with removable illuminating means, particularly by cold light, composed of light conduits 8,9 resiliently engaged in grooves 10,11 provided on the top of the frame and on the inner edges of the frame on either side of the nose, and spectacle lenses each separately provided with a small "zoom" lens 4,5 the illuminating end of said illuminating means being substantially in the axis of vision of the working field. These spectacles are useful in endoscopic micrurgy, various medical fields, in jewelry, electronics, dentistry, and for making precision assemblies and the like.

9 Claims, 2 Drawing Figures

ILLUMINATING SPECTACLES WITH VARIABLE MAGNIFYING POWER

The present invention relates to illuminating spectacles with variable magnifying power, particularly for use in micrurgy.

For delicate operations necessitating a magnification of the field of work and a good lighting, for example in micrurgy or in other fields of activity such as jewelry, clock-making, precision-assembly techniques and the like, deivces are currently used which generally ensure vision and lighting separately.

As far as vision is concerned, they are essentially composed of spectacles provided with lenses of fixed magnifying power, which the practitioner must change each time he wishes to alter the magnifying power, magnifying glasses, microscopes, monocular magnifying glasses (monocles) which are fitted in the eye socket and which, moreover, remove all notion of distance or relief. As regards the lighting of the field of work, this is effected by means of forehead mirrors pierced with two orifices to allow vision and provided with a lamp at the focus, supplied by a battery or by the mains, of helmets provided with a focussing glass receiving the "cold light" from a glass fibre conduit connected to a source of light similar to slide projectors, illuminating spectacles or the source of light of the microscopes.

More recently, a spectacle frame has been proposed, provided with a pivotable lamp casing with which are associated lenses through which a magnifying device passes, or magnifying systems, of variable spacing, held by a support and adapted to be removably engaged, with the aid of said support, on a spectacle frame provided to this end, so that each magnifying member is applied against the corresponding spectacle lens.

In this latter case, illumination is provided by a cold light emitted independently from a helmet worn by the practitioner.

In the latter known case, so-called "zoom" devices have been used as magnifying members, said "zooms" enabling the equivalent focal distance of the lens to be varied continuously in a given interval, maintaining constant the position of the image plane. The focal distance of each lens is adjusted independently by manipulating a small control lever with predetermined positions, provided for a working distances of the order of 250 to 350 mm.

The known devices present a certain number of drawbacks. They are generally bulky, not easily handled or dissociated, and, when they are designed to be more "compact", they are still unnecessarily complicated and insufficiently light. Their versatility of use by the practitioner and efficiency remain limited and their manufacturing costs may be high. Moreover, they are either inadapted to the use of cold light or require that the practitioner wears a source of cold light independent of the means of vision, this being relatively uncomfortable and not supplying the precise illumination of the work field desirable in the axis of vision.

It is an object of the invention to remedy these drawbacks and to provide illuminating spectacles with variable magnifying power, of simple, light and inexpensive construction, combining in one device means for vision and illumination, these two functions being ensured precisely, substantially in the same axis of exploration of the work field.

Another object of the invention consists in supplying said device with cold light, indispensable particularly in medical and surgical applications.

The above-mentioned objects, like others which will be more readily understood hereinbelow, are attained by a pair of illuminating spectacles with variable magnifying power, according to the invention, essentially characterised in that they comprise a frame provided with removable illuminating means, particularly by cold light, and lenses, mounted in said frame and each provided, in fixable manner, with a small "zoom" lens.

According to another feature, the illuminating means are constituted by two separate light conduits, each removabley fixable to the top of the frame, following the contour of half of the corresponding frame, from the rear end of one side to near the axis of junction of the spectacle frame, or bridge of the spectacles, and forwardly from the inner edges of the circles of the frame, on either side of the nose, the ends of the cold light conducting strands being located in the plane of the lenses and directed so as to converge at the same point as the axes of the lenses.

According to a further feature, the tops of the sides, the tops of the frame and the inner edges of the parts of the frame on either side of the nose, are provided with resilient gripping members for the removable fixing of the light conduits.

Yet another feature of the invention concerns the fixing of the "zoom" lenses to the lenses by gluing, by a technique known per se.

The invention will be more readily understood on reading the following description with reference to the accompanying drawings, in which.

Figure 1:
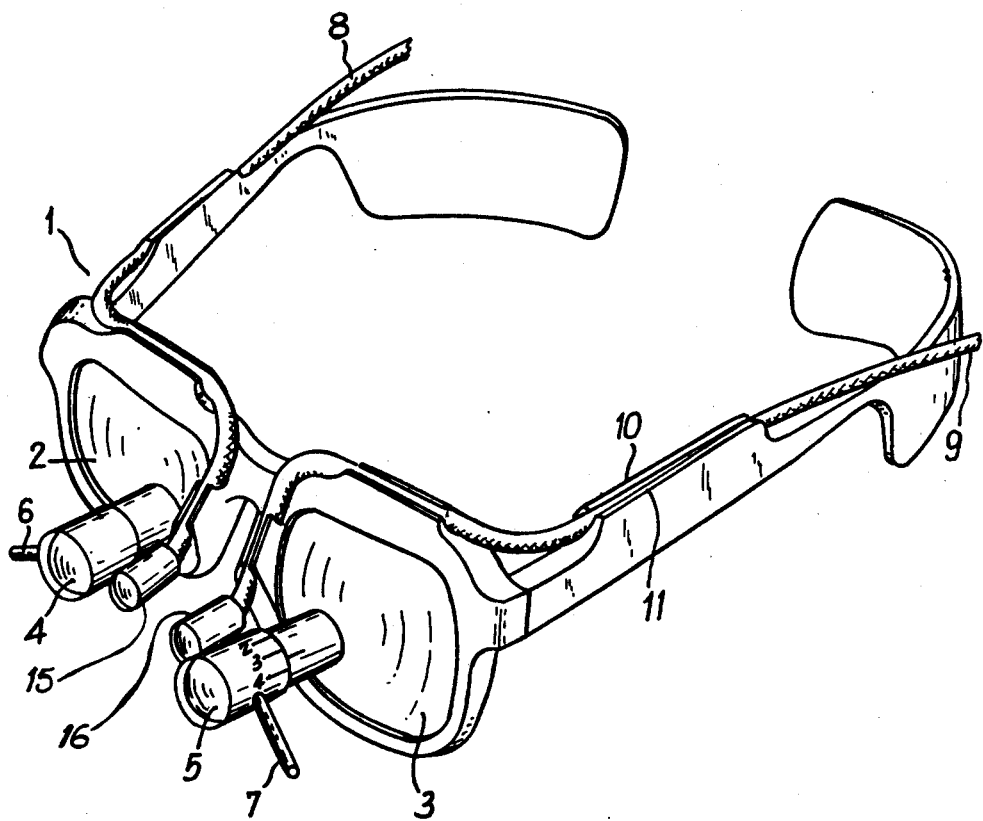
FIG. 1 shows a schematic view in perspective of the spectacles according to the invention, provided with the light conduits.
Figure 2:
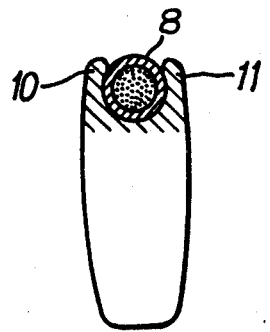
FIG. 2 is a sectional view through one side of the spectacles shown on FIG. 1.

Referring now to the drawings, FIG. 1 shows a pair of spectacles generally referenced 1, of which the frame is similar to that of conventional spectacles, and is made of light moulded material. The lenses 2,3 are optically neutral or adapted to the eyesight of the wearer and each bear a small "zoom" lens 4,5 with variable magnifying power, adjustable independently by a small lever 6,7 with predetermined positions, provided for a working distance of the order of 250 to 350 mm. The "zoom" lens is preferably connected to the corresponding lens by gluing. However, it may be connected differently, for example sealed in an opening made in the lens. Said lenses are very light and the device does not undergo any noteworthy change in weight due to this connection. It should be noted that said zoom lenses are fixed on the lenses at about 1 cm from the lower edge thereof, respecting the convergence of the eyes, as a function of the working distance mentioned hereinabove. Said zoom lenses act, in fact, on the lenses as bifocals, this advantageously enabling the practitioner to look elsewhere than in the field of operation, through the remaining part of the lenses, this, of course, being necessary, particularly in the case of corrective lenses; but also of optically neutral, protective lenses.

The light is supplied in particular by a conventional source of cold light (not shown) with two conduits 8,9 composed of glass fibre, each terminating in a focussing element 15,16; which are resiliently and removably gripped on the sides and top of the frame and in the parts of the frame on either side of the nose, in elongated, outwardly open grooves of which the walls are constituted by outward projections 10,11 from each of the two corresponding vertical faces of a side, from the top of the front of the frame, and from the parts of the frame on either side of the nose.

Said independent light conduits may either be connected to a generator (not shown), provided with two independent sources supplying a double light, or be connected by means of a Y-union to a generator with single source supplying a single light. In both cases, due to the adoption of two light conduits according to the invention, two illuminating rays or beams are obtained. Particular advantages result from this mode of construction. There is thus always one conduit in a state of functioning. In fact, if one of the conduits is damaged, it may easily and quickly be replaced by a new conduit. Connection may be effected to any slide projector with tungsten lamp by simply adapting a focussing system thereto and placing the conduit end at this point of focussing with a suitable small adapter.

It should also be noted that, if necessary, a cold light device may be replaced by a conventional low voltage device. The gripping of the electric leads in the above-mentioned grooves is then effected in the same manner as for the cold light conductors.

To ensure convenient and safe wear of the spectacles, they may comprise enveloping sides, with the required flexibility at the hinge and at the rear of the head, as shown in FIG. 1; this nonlimiting arrangement advantageously avoids any forward slide of the spectacles.

Of course, the invention may be carried out according to other variants or modifications, without departing from the scope of the invention. As may be understood from the above description, the invention provides the proposed lenses by offering a combination of the illumination and variable magnifying power on the same device, with two illuminating beams, particularly in cold light, focussed substantially in the axis of vision, allowing a precise exploration of the field of operation, a versatility of use and easy and light wear by the practitioner who may put them on and instantaneously change the light conduits and rapidly and precisely adjust the magnifying power of the "zoom" lenses, independently.

We claim:

1. In a pair of spectacles wherein a frame means includes a pair of transparent members disposed before the respective eyes of a wearer, the combination including two optical magnifying means supported on said frame means with their optical axes arranged to converge, and a source of cold light terminating in focussing means to direct said light in the plane of the convergent axes of said optical magnifying means and to concentrate it at the point of said convergence.

2. A device as claimed in claim 1 wherein the means for emitting cold light are constituted by a light wave guide, of the type made of glass fibres, one end being provided with a focussing element disposed at the level of the two lenses.

3. A device as claimed in claim 1, wherein the optical means are constituted by adjustable lenses with variable magnifying power, of the "zoom" type.

4. A device as claimed in claim 3, wherein the lenses with variable magnifying power of the "zoom" type, are connected to the transparent members by gluing.

5. A device as claimed in claim 3, wherein the lenses with variable magnifying power of the "zoom" type, are connected to the lens by sealing in openings made in said lenses.

6. A device as claimed in claim 1 wherein the illuminating means are constituted by two light conduits, of the glass fibre light wave guide type, supplied with cold light, each of these conduits passing along the frame means from the rear end of each side, each conduit having a first bend to follow a path in the direction of the nose, each conduit having a second bend to follow a path bringing the end of the conduit to the level of the plane defined by the two optical magnifying means, each of the conduits terminating, by means of a terminal bend, in a focussing member located in the plane of the magnifying means, the two focussing members being directed so as to converge at the same point as the axes of the magnifying means.

7. A device as claimed in claim 1 wherein the respective upper parts of the sides of the frame means and the inner edges of the frame means on either side of the nose are provided with resilient gripping means adapted to removably hold the light conduits.

8. A device as claimed in claim 7, wherein said resilient gripping means are constituted by a groove along the upper edge of each side, the upper edge of the lens frame and the inner edge of this frame on either side of the nose, this groove being arranged so as to receive and resiliently hold the light conduits.

9. A device as claimed in claim 1, wherein the sides of the spectacles are extended rearwardly by a portion curved towards the centre and adapted to envelope the rear of the head so as to avoid any forward sliding of the spectacles.

* * * * *